United States Patent [19]

Rambo et al.

[11] Patent Number: 5,368,560
[45] Date of Patent: Nov. 29, 1994

[54] SUCTION NOZZLE

[75] Inventors: Robert D. Rambo, Sellersville, Pa.; John Yorke, Canastota, N.Y.

[73] Assignee: Medical Development Systems, Inc., Colmar, Pa.

[21] Appl. No.: 38,860

[22] Filed: Mar. 29, 1993

[51] Int. Cl.⁵ .............................................. A61M 1/00
[52] U.S. Cl. ...................................... 604/35; 604/902
[58] Field of Search ............... 433/91, 93, 96; 15/420, 15/422, 422.1; 604/902, 35, 39, 43, 44, 48, 73, 93, 119

[56] References Cited

U.S. PATENT DOCUMENTS

| | | | |
|---|---|---|---|
| 3,828,780 | 8/1974 | Morrison | 128/275.1 |
| 4,248,219 | 2/1981 | Moore, Jr. et al. | 604/119 |
| 4,719,914 | 1/1988 | Johnson | 128/303.1 |
| 4,735,603 | 4/1988 | Goodson et al. | 604/21 |
| 4,792,327 | 12/1988 | Swartz | 604/22 |
| 4,886,492 | 12/1989 | Brooke | 604/49 |
| 5,055,100 | 10/1991 | Olsen | 604/22 |

FOREIGN PATENT DOCUMENTS 2350945 10/1973 Germany ............... 604/119

Primary Examiner—Jerome L. Kruter
Attorney, Agent, or Firm—Charles S. McGuire

[57] ABSTRACT

A suction nozzle for attachment to a partial vacuum source for removing smoke and liquid from a surgical area during laser or electrocautery surgery. The nozzle includes a cylindrical inner tube fixedly and concentrically attached within a cylindrical outer tube with the distal end of the inner tube extending forwardly of the distal end of the outer tube. A plurality of annularly spaced, radially extending connecting webs interconnect the outer and inner tubes together and define a respective plurality of discreet passageways through which the smoke and liquid are suctioned in addition to the passageway of the inner tube. An auxiliary nozzle may be attached to the exposed, distal end of the inner tube for passage through a trocar cannula or the like during endoscopic procedures. A flow control knob is also provided for removable and rotatable attachment to the distal end of the outer tube for selectively controlling the fluidics flow through the passageways between the connecting webs.

8 Claims, 3 Drawing Sheets

SUCTION NOZZLE

BACKGROUND OF THE INVENTION

This invention relates to suction nozzles and, more particularly, to a nozzle for use on the distal end of a suction tube for removal of smoke and liquid matter from a laser or electrocautery surgical area.

It has become generally well known in the medical industry that smoke created during electrocautery and laser surgeries is offensive and probably dangerous and should be immediately removed from the surgical site. The smoke, or "plume" as it is sometimes referred to in the industry, is created from the decomposition of organic material of the tissue which has been ablated by the electric current and/or laser beam at the control of the surgeon. Electrocautery and laser surgeries may be conducted either in conjunction with a laparoscope, or other type of endoscopic instrument, or in open surgery with the surgical site of the patient's inner body in direct view and directly accessible to the surgeon. During endoscopic surgery, smoke and liquid removal must occur through a cannula while open surgery permits smoke and liquid removal in close yet variable proximity to the open surgical site.

Many of the known smoke removal systems are integrated with electro-surgical instruments such as may be seen in U.S. Pat. No. 5,055,100 issued to Olsen on Oct. 8, 1991; U.S. Pat. No. 4,719,914 issued to Johnson on Jan. 19, 1988; and U.S. Pat. No. 3,828,780 issued to Morrison, Jr. on Aug. 13, 1974. A closed circuit smoke removal system may be seen in U.S. Pat. No. 4,735,603 issued to Goodson et al on Apr. 5, 1988 which is used to remove smoke during laparoscopic surgery involving recirculation of $CO_2$ gas through the surgical site cavity including filtering means and means to maintain pressure for proper abdominal distention of the patient. Lastly, other types of suction and filtering apparatus used primarily for solid/liquid removal rather than smoke removal may be seen in U.S. Pat. Nos. 4,792,327 issued to Swartz on Dec. 20, 1988 and 4,886,492 issued to Brooke on Dec. 12, 1989.

SUMMARY OF THE INVENTION

It is a principal object of the present invention to provide a suction nozzle for use in combination with a surgical smoke evacuation system which includes two concentric suction tubes through which smoke and liquid are drawn.

It is another object of the present invention to provide a suction nozzle of the above type in which the inner tube extends beyond the outer tube which thereby divides the suction force and substantially prevents the accidental suctioning of soft tissue, cotton, sponges, etc., through either one or both of the tubes.

It is a further object of the present invention to provide a suction nozzle which removes smoke and liquid from a surgical site about a larger radius than suction nozzles of the single channel type.

It is still another object of the present invention to provide a suction nozzle which can be used in both open surgeries and through a cannula during endoscopic surgeries.

It is yet a further object of the present invention to provide a suction nozzle having a separate auxiliary flow control knob for use in combination with a suction tube of small diameter positioned at the distal end of the inner tube when suctioning through a cannula.

Other objects will in part be obvious and in part appear hereinafter.

In accordance with the foregoing objects, the invention comprises a gaseous and liquid suction nozzle which is attached to the distal end of a suction tube whose proximal end is attached to a partial vacuum source. The nozzle is intended primarily for use in the operating room during laser and electrocautery surgical procedures to draw smoke and liquid matter through the nozzle and the suction tube to which the nozzle is attached. The partial vacuum source may include a smoke filter and liquid containment unit such as the type described and claimed in my presently copending application Ser. No. 08/038,838. The nozzle is hand-held by a nurse and directed at the smoke and liquid matter present in the surgical area as required.

The nozzle is formed of a rigid plastic and is generally cylindrical in shape. The nozzle includes a cylindrical outer tube with a first, proximal length thereof having a first, constant diameter for the insertion thereof into the distal, open end of a length of flexible suction tubing. Prior to insertion into the distal end of the suction tubing, the proximal length of the nozzle is coated with an adhesive to ensure a tight, permanent seal therebetween. A second, distal length of the nozzle outer tube integrally and linearly extends from and has a second diameter somewhat larger than the diameter of the proximal length. The proximal and distal lengths of the outer tube are integrally connected by a tapering segment which includes a plurality of longitudinally extending, annularly spaced ribs.

The nozzle further includes a rigid length of small diameter tube (i.e., approx. ¼") which is concentrically positioned within and connected to the distal length of the nozzle outer tube by a plurality of radially extending, annularly spaced connecting webs. The inner tube extends from a point slightly forward of the tapering segment, to a position beyond the distal edge of the nozzle outer tube. The gaseous and liquid matter is thus drawn through the inner tube as well as between the inner tube and the nozzle outer tube in which the inner tube is positioned. The provision of a concentric inner tube divides the vacuum force into separate air currents about the distal ends of the concentric inner and outer tubes. This feature allows for a larger radius of gas to be drawn into the nozzle than is possible with suction nozzles having a single nozzle channel. Also, accidental suctioning of the patient's bodily tissue, sponges, cotton, etc. into the nozzle is substantially prevented. Furthermore, since the inner tube extends forwardly of the outer tube, the possibility that both would be accidentally and simultaneously blocked by contact with foreign debris and/or the patient's tissue is substantially decreased.

DETAILED DESCRIPTION

Figure 1:
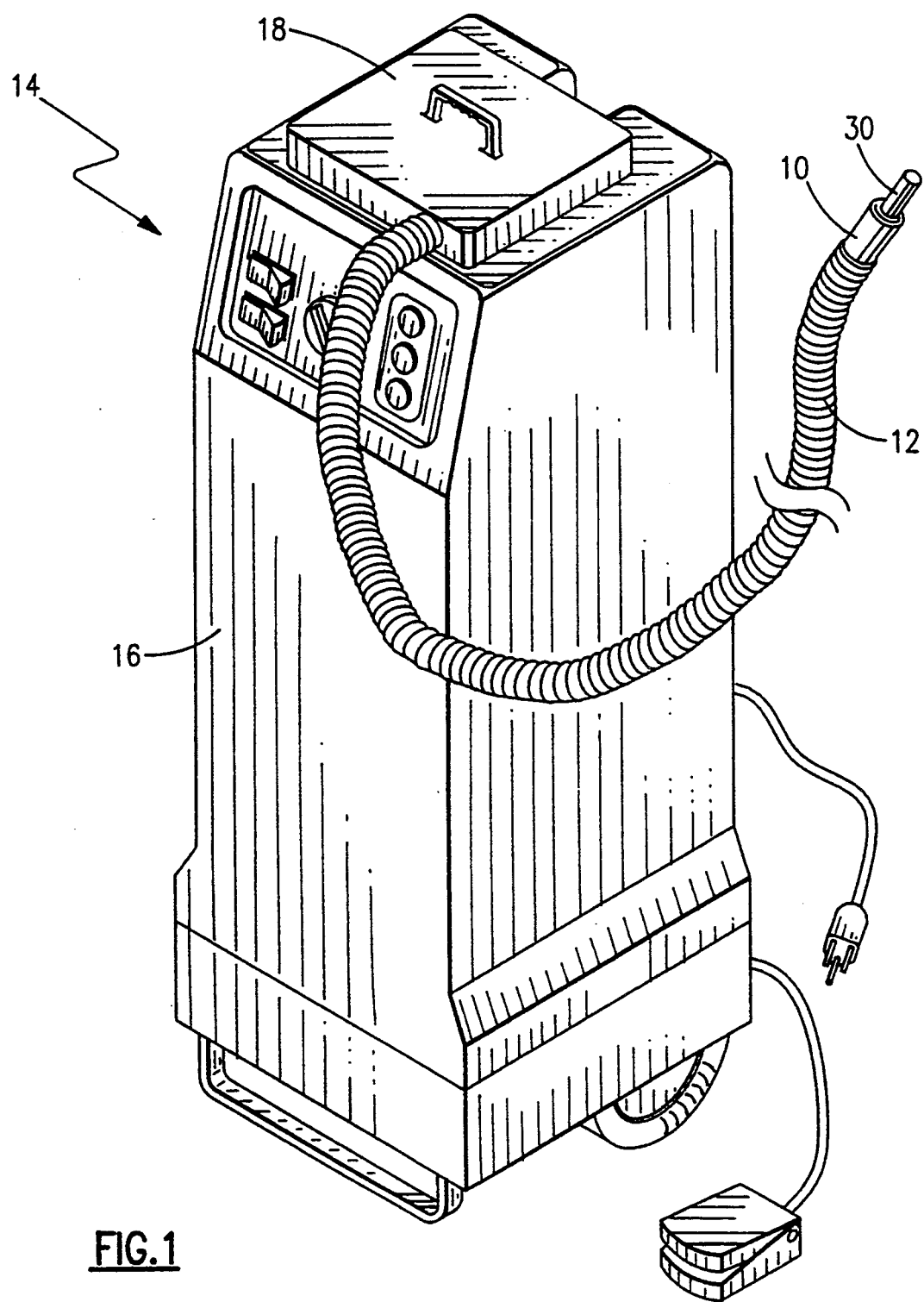
FIG. 1 is a perspective view of a gaseous filter and liquid containment system having the first end of a length of suction tubing attached thereto with the suction nozzle attached to the second, free end thereof.
Figure 2:
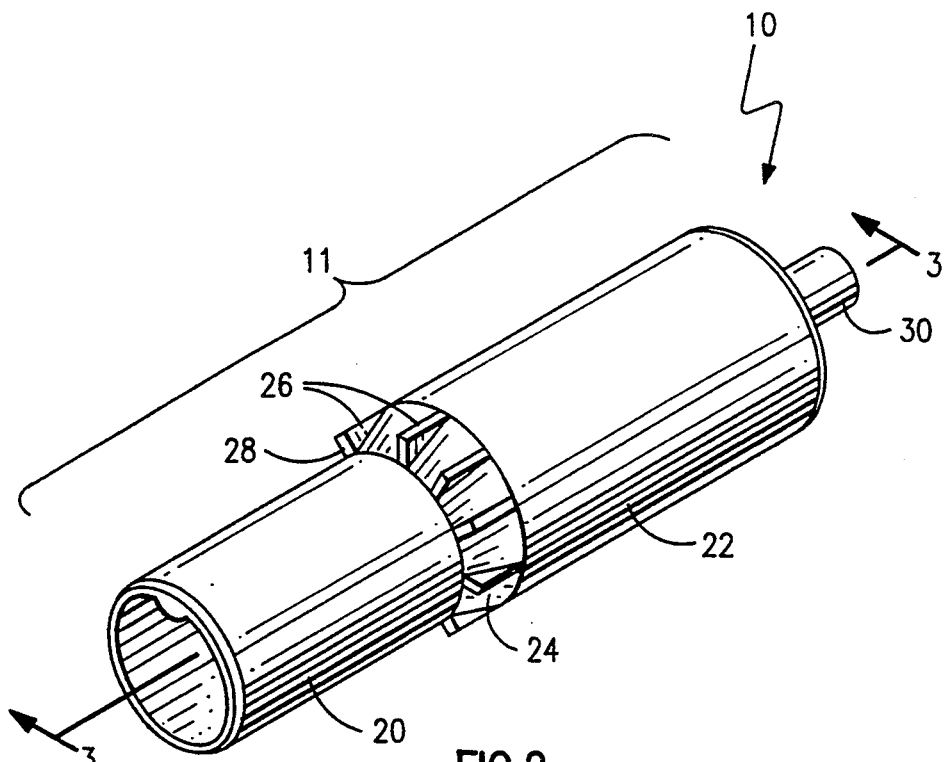
FIG. 2 is a perspective view of the suction nozzle seen attached to the free end of the suction tubing in FIG. 1.
Figure 4:
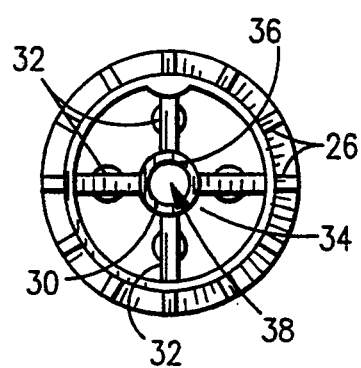
FIG. 4 is a plan view of the proximal end thereof.
Figure 5:
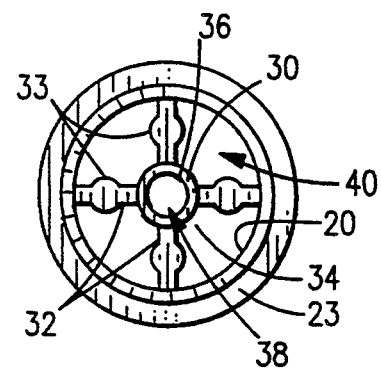
FIG. 5 is a plan view of the distal end thereof.

Referring now to the drawings, there is seen in FIG. 1 the inventive suction nozzle 10 attached to the end of a length of flexible tubing 12. The opposite end of tubing 12 is attached to a representative gaseous filter and liquid containment system denoted generally by the reference numeral 14. Gaseous filter and liquid containment system 14 is intended for use in hospital operating rooms to remove smoke and unwanted liquid matter produced at a surgical area by electrocautery and laser surgeries. A nurse manually grasps nozzle 10 and directs it at the surgical area. A partial vacuum source (not shown) is housed within cabinet 16 to draw the smoke and liquid matter consecutively into and through nozzle 10, suction tubing 12 and a filter unit 18 which is removably seated within the top of cabinet 16. Liquid matter is captured in filter unit 18 while smoke is drawn and filtered therethrough and allowed to dissipate into the ambient air.

Referring to FIGS. 2–5, nozzle 10 is seen to have a generally cylindrically shaped outer tube 11 having a first, proximal length 20 having an outer diameter $d_1$ and a length $l_1$. A second, distal length 22 integrally extends from proximal length 20 and has an outer diameter $d_2$ and length $l_2$, both of which are slightly larger than respective diameter $d_1$ and length $l_1$ of proximal length 20. Proximal and distal lengths 20 and 22, respectively, are connected by a segment 24 which tapers outwardly from proximal length 20 to distal length 22. A plurality of wedge-shaped ribs 26 are integrally formed in annularly spaced relationship about tapering segment 20.

Figure 3:
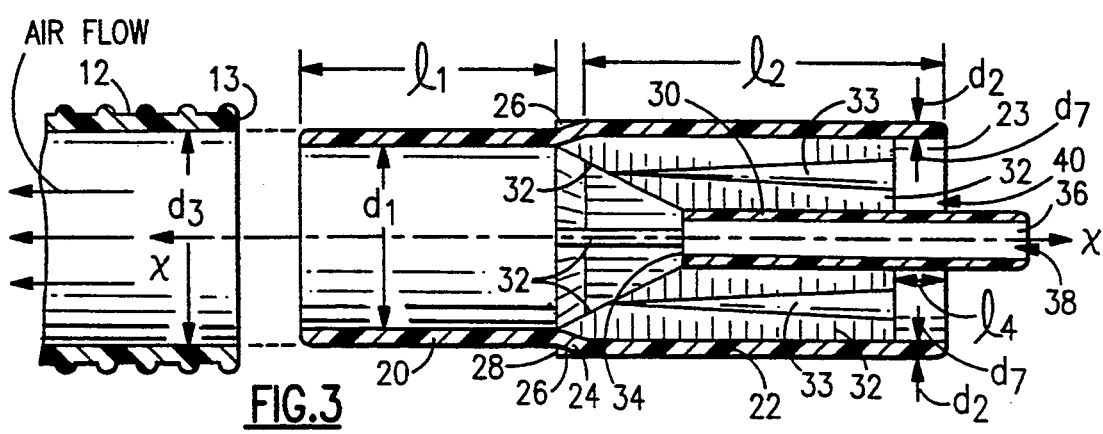
FIG. 3 is a longitudinal cross-section of the nozzle as taken along the line 3—3 in FIG. 2.

As seen best in FIG. 3, ribs 26 are in the form of right angles with an edge 28 hereof extending perpendicular to the longitudinal axis x—x along which outer tube 11 lies. Edge 28 of each rib 26 provides a stop against which the distal edge 13 of suction tubing 12 is abutted upon insertion of nozzle proximal length 20 therein. Suction tubing 12 has an inner diameter $d_3$ which is slightly larger than the outer diameter $d_1$ of proximal length 20 thereby providing a secure friction fit therebetween upon inserting the latter into the former. A liquid adhesive may also be applied to the outer surface of proximal length 20 prior to insertion to fixedly attach nozzle 10 to suction tubing 12 and ensure an air-tight seal therebetween.

A rigid, generally cylindrically shaped inner tube 30 is concentrically positioned within distal length 22 and is fixedly attached thereto by four radially extending, annularly spaced connecting webs 32. Inner tube 30 tapers gradually inwardly less than 1° from the proximal end 34 thereof to the distal end 36 thereof. Inner tube proximal end 34 is positioned within distal length 22 between tapering segment 24 and the terminal edge 23 of distal length 22. Inner tube 30 extends forwardly of terminal edge 23 such that distal, open end 38 of inner tube 30 is positioned forwardly of the distal, open end 40 of distal length 22. The vacuum force occurs at both open ends 38 and 40 of inner tube 30 and distal length 22, respectively, thereby drawing gaseous and liquid matter therethrough and into proximal length 20 and suction tubing 12. Furthermore, since open end 38 of inner tube 30 is positioned forwardly of open end 40 of distal length 22, separate eddy currents are established thereabout which cause a relatively large gaseous area to be suctioned.

Connecting webs 32 are seen to include a bulbous center portion 33 which extends and tapers rearwardly inwardly the full longitudinal lengths thereof. Since nozzle 10 is a molded piece, bulbous center portions 33 have been provided to assist the ejector pin when removing the nozzle 10 from the mold (not shown). It will also be noticed that webs 32 linearly extend from the proximal end 34 of inner tube 30 to the juncture of proximal length 20 and tapering segment 24.

Gaseous and liquid matter is thus drawn into nozzle 10 through the passageways between inner tube 30 and outer tube 11 between each web 32, and also through inner tube 30 for a total of five discrete passageways at distal length 22 leading to the passageway at proximal length 20. The provision of a plurality of discrete passageways as well as inner tube 30 extending forwardly of distal length 22 has many advantages. For instance, the accidental suctioning of sponges, cotton, etc, is substantially eliminated since there is no one passageway at distal length 22 large enough to pass these items. Also, it is virtually impossible to accidentally block each of the five passageways at the same time by inadvertent contact of the nozzle with the patient's tissue. An example of how easily this occurs with a single passageway nozzle is placing the palm of a hand over the nozzle of a vacuum cleaner hose. Should this occur with the gaseous and liquid containment system 14 of FIG. 1, the system would falsely sense full occlusion of filter 18 and shut itself down. Conversely, placing a hand (or the patient's skin) in contact with nozzle 10 would first contact and block inner tube 30 while allowing gaseous and liquid matter to continue to be drawn through the four passageways defined by webs 32 between distal length 22 and inner tube 30.

Figure 6:
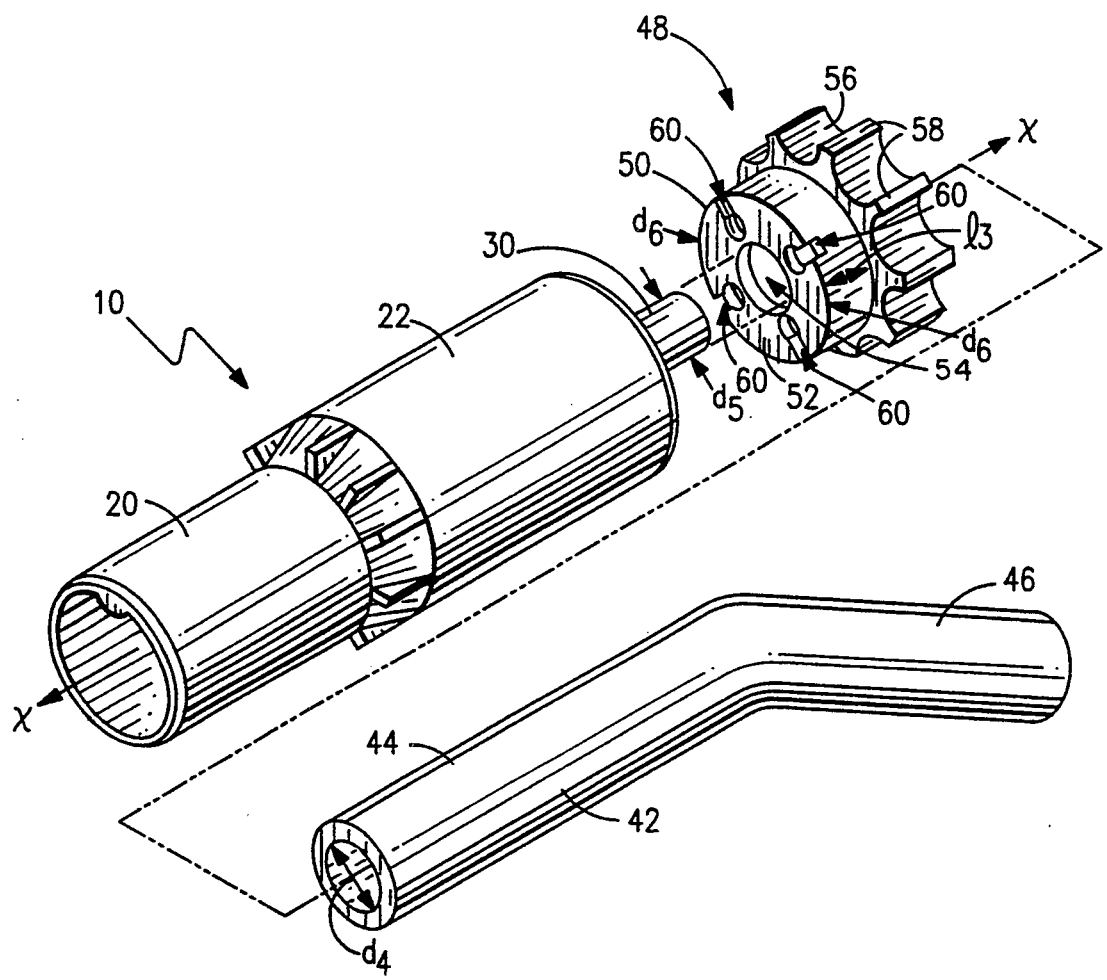
FIG. 6 is the view of FIG. 2 and further showing the auxiliary flow control knob and auxiliary nozzle in spaced relation thereto.

As aforementioned, nozzle 10 may be used in open surgery as well as endoscopic surgery. In open surgery, nozzle 10 is positioned in close yet variable proximity to the surgery area. Endoscopic surgery occurs through a cannula or the like which has been inserted through an incision in the patient's skin. The laser/electro-cautery plume thus emanates internally of the patient with removal thereof having to take place through the cannula. Attention is turned to FIGS. 6–8 which show an auxiliary nozzle and flow control knob for use in endoscopic surgery.

In particular, auxiliary nozzle 42 may be either rigid or flexible and has an internal diameter $d_4$ which is only slightly larger than the outer diameter $d_5$ of the distal, exposed end of inner tube 30. Auxiliary nozzle 42 is removably attached at a first end 44 thereof to the distal, exposed end of inner tube 30 by a friction fit between the two. The opposite, open end 46 thereof is passed into a cannula (not shown) to enter the patient's body at the surgical area and draw the plume and liquid matter therefrom.

Since all gaseous and liquid matter removal occur through inner tube 30 in this instance, it is desirable to close off the four passageways between ribs 32. Thus, prior to attachment of auxiliary nozzle 42 to inner tube 30, flow control knob 48 is removably and rotatably mounted to nozzle 10. Knob 48 permits selective adjustment of the amount of vacuum force occurring at inner tube 30 by closing off the four passageways defined by webs 32 between inner tube 30 and distal length 22. Knob 48 is formed as a single molded piece and includes a cylindrical base portion 50 having a planar bottom wall 52 and an outer diameter $d_6$ which is slightly smaller than the inner diameter $d_7$ of distal length 22 (FIG. 3). Bottom wall 52 includes a centrally located aperture 54 having a diameter $d_8$ (FIG. 6) which is slightly larger than the outer diameter $d_5$ of inner tube 30 and thus substantially the same as the inner diameter $d_4$ of auxiliary nozzle 42. Thus, knob 48 is removably mounted to nozzle 10 by inserting inner tube 30 through aperture 54 in bottom wall 52.

Knob 48 further includes circular portion 56 having annularly spaced, longitudinally extending ribs 58 which is integrally formed with base portion 50. Also, an inner wall 59 of constant diameter extends the full longitudinal length of knob 48 from the top surface of circular portion 56 to bottom wall 52. Circular portion 56 has a maximum diameter $d_9$ which is larger than diameter $d_6$ of base portion 50 and substantially the same as outer diameter $d_2$ of distal length 22. The length $l_3$ of base portion 50 as measured from the outwardly facing surface of bottom wall 52 to circular portion 56 is slightly longer than the length $l_4$ of distal length 22 as measured from the distal edges of webs 32 to the distal edge 23 of distal length 22. Thus, when mounted to nozzle 10, base portion 50 of knob 48 extends within distal length 22 with bottom wall 52 in abutting contact with the distal edges of webs 32. Also, circular portion 56 is positioned longitudinally adjacent distal length 22 with ribs 58 thereof being exposed. Since nozzle 10 and knob 48 are both formed from smooth plastic, the coefficient of friction between the outwardly facing wall of circular portion 50 and the inwardly facing wall of distal length 22 at length $l_4$ is low. Knob 48 may thus be manually rotated about axis x—x within distal length 22 by using the thumb against circular portion 56 and ribs 58.

Figure 7:
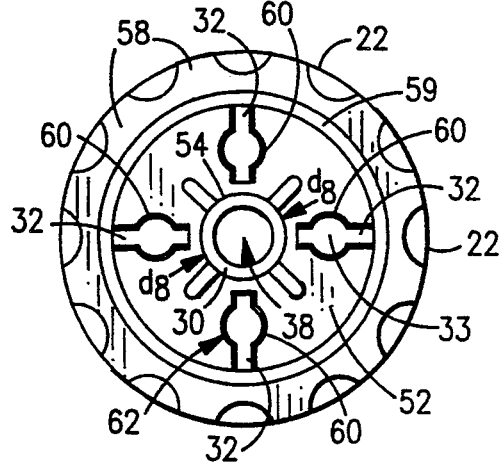
FIG. 7 is a plan view of the flow control knob shown attached to the distal end of the nozzle with the control knob rotated to the fully closed position.
Figure 8:
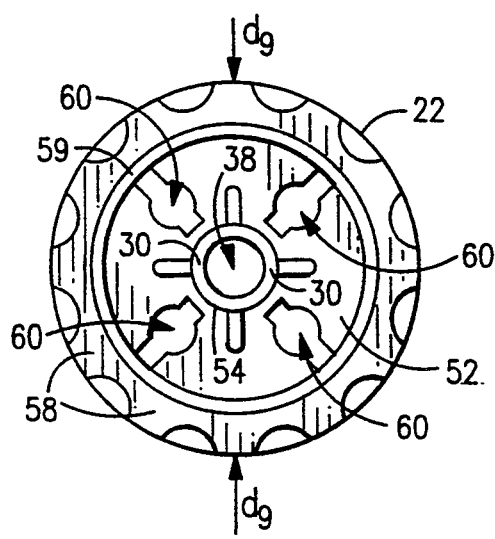
FIG. 8 is the view of FIG. 7 showing the knob rotated to the fully open position.

In this regard, bottom wall 52 is seen to include four radially extending, annularly spaced apertures 60 which align with and are in the shape of a lateral cross-section of webs 32. FIG. 7 illustrates a plan view of knob 48 mounted to distal length 22 with webs 32 and apertures 60 in full alignment. In this position, it will be noticed that the four passageways of nozzle 10 defined by webs 32 are closed except for a small gap 62 remaining between each web 32 and aperture 60. Thus, substantially most of the vacuum force occurs at inner tube 30 with the force being adjustable by selectively rotating knob 48 between the fully closed position seen in FIG. 7, to the fully open position seen in FIG. 8 where apertures 60 are in full communication with the four passageways of nozzle 10 between webs 32.

As discussed above, auxiliary nozzle 42 is removably attached to the distal end of inner tube 30 following mounting of knob 48 thereon. Knob 48 is rotated to achieve the desired vacuum force through inner tube 30. The distal end 46 of auxiliary nozzle may then be inserted through the cannula into the patient's body to remove gaseous and liquid matter therefrom generated by the laser or electrocautery surgery.

What is claimed is:

1. A nozzle for attachment to a partial vacuum source to draw gaseous and liquid matter through said nozzle from a surgical area, said nozzle comprising:

a) a first elongated, cylindrical, outer tube having open distal and proximal ends with at least one discreet passageway leading from said distal to said proximal end with said proximal end attached to and in fluid communication with said partial vacuum source, said outer tube having a proximal length and a distal length with said proximal length having a diameter slightly smaller than the diameter of said distal length, said proximal and distal lengths being interconnected by an integral segment which tapers outwardly from said proximal to said distal length, said inner tube proximal length being positioned between said outer tube distal end and said integral segment said distal end directed at said surgical area with said gaseous and liquid matter being drawn through said at least one discreet passageway;

b) a second elongated, inner tube having respective open distal and proximal ends with a second discreet passageway leading from said inner tube distal end to said inner tube proximal end, said inner tube distal end being positioned forwardly and exteriorly of said outer tube distal end, said inner tube proximal end being positioned between said outer tube proximal and distal ends; and c) means fixedly attaching said inner tube concentrically within said outer tube with said second discreet passageway in fluid communication with said at least one discreet passageway, said means comprising a plurality of annularly spaced connecting webs having respective proximal and distal edges and radially extending from said outer tube to said inner tube thereby defining a respective plurality of discreet passageways therebetween, said plurality of discreet passageways being in fluid communication with said at least one discreet passageway.

2. The invention according to claim 1 wherein said proximal edges of said connecting webs extend from said proximal end of said inner tube to the juncture of said proximal length and said integral segment.

3. The invention according to claim 2 wherein said distal edges of said connecting webs extend from said inner tube to said outer tube in a direction substantially parallel to and spaced a predetermined distance from said outer tube distal end.

4. The invention according to claim 3 and further including a plurality of ribs annularly spaced about said integral segment, said ribs being in the shape of a right triangle with an edge thereof extending in a plane parallel to said distal edges of said connecting webs.

5. The invention according to claim 4 and further comprising an auxiliary nozzle comprising an elongated tube having first and second, open ends with said first end having an inner diameter $d_4$ which is slightly larger than the outer diameter $d_5$ of said distal end of said inner tube, said auxiliary nozzle first end removably attached to said distal end of said outer tube.

6. The invention according to claim 5 and further comprising a flow control knob romovably and rotatably mounted to said outer tube distal end, said knob being rotatably movable between a fully closed position wherein portions thereof substantially block said plurality of discreet passageways from ambient pressures, to a fully open position wherein said plurality of discreet passageways are vented to said ambient pressures.

7. The invention according to claim 6 wherein said flow control knob includes a cylindrical base portion having a bottom wall and an integral circular portion extending from said base portion opposite said bottom wall, said circular portion including a plurality of annularly spaced ribs having a maximum diameter $d_9$ substantially the same as said diameter of said distal end of said outer tube, said bottom wall including a centrally located aperture wherethrough said distal end of said inner tube extends, said cylindrical portion having a diameter $d_6$ which is slightly smaller than the inner diameter $d_7$ of said outer tube distal end, and said cylindrical portion having a length $l_3$ which is slightly longer than said length $l_4$ between said distal end of said outer tube and said distal edges of said connecting webs, whereby said cylindrical portion is removably inserted within said outer tube distal end with said bottom wall in abutting contact with said distal edges of said connecting webs and said circular portion lying longitudinally adjacent to said outer tube distal end with said circular portion ribs being accessible for manual engagement to selectively rotate said knob within said proximal length of said outer tube.

8. The invention according to claim 7 wherein said bottom wall further includes a plurality of radially extending apertures, each having substantially the same outline as a lateral cross section of one of said connecting webs, said radially extending apertures being in substantially the same spatial relationship about said bottom wall as said connecting webs are about said outer tube whereby said apertures are in alignment with said distal edges of said connecting webs when said knob is rotated to said fully closed position.

* * * * *